United States Patent
Gale et al.

(10) Patent No.: US 9,439,788 B2
(45) Date of Patent: *Sep. 13, 2016

(54) STENT LOCKING ELEMENT AND A METHOD OF SECURING A STENT ON A DELIVERY SYSTEM

(71) Applicant: Abbott Cardiovascular Systems Inc., Santa Clara, CA (US)

(72) Inventors: David C. Gale, Kennesaw, GA (US); Klaus Kleine, Los Gatos, CA (US); Anthony J. Abbate, Santa Clara, CA (US); Bin Huang, Pleasanton, CA (US); Svava Maria Atladottir, Mountain View, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/056,887

(22) Filed: Oct. 17, 2013

(65) Prior Publication Data
US 2014/0107759 A1    Apr. 17, 2014

Related U.S. Application Data

(62) Division of application No. 10/879,328, filed on Jun. 28, 2004, now Pat. No. 8,568,469.

(51) Int. Cl.
| | |
|---|---|
| *A61F 2/06* | (2013.01) |
| *A61F 2/82* | (2013.01) |
| *A61F 2/91* | (2013.01) |
| *A61F 2/958* | (2013.01) |
| *A61F 2/915* | (2013.01) |
| *A61F 2/95* | (2013.01) |

(52) U.S. Cl.
CPC . *A61F 2/82* (2013.01); *A61F 2/91* (2013.01); *A61F 2/958* (2013.01); *A61F 2002/91558* (2013.01); *A61F 2002/91583* (2013.01); *A61F 2002/91591* (2013.01); *A61F 2002/9505* (2013.01); *A61F 2220/0033* (2013.01)

(58) Field of Classification Search
CPC ............ A61F 2002/9505; A61F 2002/91558; A61F 2002/91583; A61F 2/82; A61F 2/91; A61F 2220/0033; A61F 2/958; A61F 2002/91591
USPC ........... 623/1.15, 1.16, 2.11, 2.14, 2.17, 2.18
See application file for complete search history.

(56) References Cited

U.S. PATENT DOCUMENTS

2002/0120323 A1* 8/2002 Thompson ................ A61F 2/91
                                                                 623/1.11

* cited by examiner

*Primary Examiner* — Jing Ou
(74) *Attorney, Agent, or Firm* — Squire Patton Boggs (US) LLP (57) ABSTRACT

A stent with a stent locking element and a method of securing a stent on a delivery implement, such as a catheter are disclosed. The locking element can include coupling elements capable of being releasably coupled to one another. The coupling elements may be adapted to inhibit shifting of the stent on the delivery implement. In some embodiments, the releasably coupled elements may secure the stent on the delivery implement.

27 Claims, 6 Drawing Sheets

STENT LOCKING ELEMENT AND A METHOD OF SECURING A STENT ON A DELIVERY SYSTEM

This application is a division of U.S. application Ser. No. 10/879,328 filed Jun. 28, 2004, now U.S. Pat. No. 8,568,469, which application is hereby incorporated herein by reference.

BACKGROUND OF THE INVENTION

1. Field of the Invention

This invention relates to a stent having a locking element and a method of securing a stent on a delivery system such as a catheter.

2. Description of the State of the Art

This invention relates to radially expandable endoprostheses which are adapted to be implanted in a bodily lumen. An "endoprosthesis" corresponds to an artificial implantable medical device that is placed inside the body. A "lumen" refers to a cavity of a tubular organ such as a blood vessel. These endoprostheses are commonly referred to as stents. Stents are generally cylindrically shaped devices which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty or valvuloplasty) with apparent success.

Stents have been made of many materials including metals and polymeric materials such as plastic, including biodegradable plastic materials. Stents have been formed from wire, tube stock, etc. Stents have also been made from sheets of material which are rolled into a cylindrical shape. A medicated stent may be fabricated by coating the surface of either a metal or polymeric scaffolding or substrate with a polymeric carrier that includes an active agent or drug. In addition, the structure of a stent is typically composed of a pattern that allows the stent to be radially expandable. The pattern should be designed to maintain the necessary longitudinal flexibility and radial rigidity of the stent. Longitudinal flexibility facilitates delivery of the stent and radial rigidity is needed to hold open a bodily lumen.

A treatment involving a stent involves both delivery and deployment of the stent. "Delivery" refers to introducing and transporting the stent through a bodily lumen to a region requiring treatment. "Deployment" corresponds to the expanding of the stent within the lumen at the treatment region. Delivery and deployment of a stent can be accomplished, for example, by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. The stent is then expanded by inflating the balloon. The balloon may then be deflated and the catheter withdrawn. In the case of a self-expanding stent, the stent may secured to the catheter via a retractable sheath or a sock. When the stent is in a desired bodily location, the sheath may be withdrawn allowing the stent to self-expand. A potential shortcoming of the foregoing methods of securing a stent is that the sheath or sock increases the form factor or profile of the stent. Since delivery is facilitated by a small profile and flexibility, an increase in form factor tends to impede delivery of the stent to a desired location in the bodily lumen.

A number of techniques have been suggested for the fabrication of stents from sheets and tubes. One such technique involves laser cutting or etching a pattern onto a material. Laser cutting may be performed on a sheet of material which is then rolled into a tube. Alternatively, a desired pattern may be etched directly onto a tube. Fabricating a stent from a tube is preferable due to time and cost considerations. Other techniques involve cutting a desired pattern onto a sheet or a tube via chemical etching or electrical discharge machining Laser cutting of stents has been described in a number of publications including U.S. Pat. No. 5,780,807 to Saunders, U.S. Pat. No. 5,922,005 to Richter, and U.S. Pat. No. 5,906,759 to Richter.

SUMMARY OF THE INVENTION

The present invention is directed to a stent locking element and a method of securing a stent on a delivery implement, such as a catheter. The locking element can include a first coupling element and a second coupling element capable of being releasably coupled to the first coupling element. The coupling elements are adapted to inhibit shifting of the stent on the delivery implement. A method is also disclosed that includes positioning a stent over a delivery implement. Some embodiments may include releasably coupling the first coupling element to the second coupling element to secure the stent on the delivery implement.

DETAILED DESCRIPTION OF THE INVENTION

The method described herein may be particularly useful for implantable medical devices in which at least a portion of the surface of the implantable medical device is polymeric. For example, an implantable medical device may be fabricated partially or completely from a purified biodegradable, bioabsorbable, or biostable polymer. The term "biodegradable" refers to polymers that are capable of being completely degraded and/or eroded when exposed to bodily fluids such as blood and can be gradually resorbed, absorbed and/or eliminated by the body. "Biodegradable" is intended to broadly include biologically erodable, bioabsorbable, and bioresorbable polymers as well as other types of polymers that are broken down and/or eliminated by the body. In addition, a polymer-fabricated device may serve as a substrate for a polymer-based coating. The polymer-based coating may contain, for example, an active agent or drug for local administration at a diseased site. Instead of or in addition to the drug delivery coating, an active agent or a drug can be incorporated into a body of a polymer-fabricated device.

Alternatively, the implantable medical device may include a non-polymer substrate with a polymer-based coating. The substrate may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Although the embodiments of the invention have been described with reference to a stent, other types of implantable medical devices, including grafts and stent-grafts, are also within the scope of the invention. The geometry of the body, whether polymeric or not, may be of virtually any design.

Representative examples of polymers that may be used to fabricate an implantable medical device using the methods disclosed herein include poly(N-acetylglucosamine) (Chitin), Chitoson, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

Examples of active agents or drugs include immunosuppressive substances such as rapamycin and structural derivatives or functional analogs thereof, such as 40-O-(2-hydroxy)ethyl-rapamycin (known by the trade name of Everolimus available from Novartis), 40-O-tetrazole-rapamycin, 40-O-(3-hydroxy)propyl-rapamycin and 40-O-[2-(2-hydroxy)ethoxy]ethyl-rapamycin; and antiproliferative substances such as actinomycin D, or derivatives and analogs thereof. Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, docetaxel, methotrexate, azathioprine, vincristine, vinblastine, fluorouracil, doxorubicin, hydrochloride, and mitomycin. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin. Examples of such cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil ($\omega$-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon; genetically engineered epithelial cells; tacrolimus; and dexamethasone.

Figure 1:
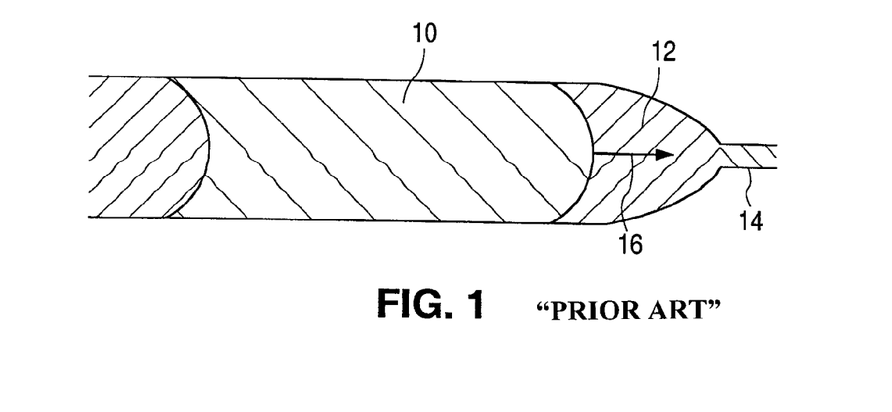
FIG. 1 depicts a diagram of a stent positioned on balloon.

A potential problem in delivery of an implantable medical device, such as a stent, is retention of the device on a delivery implement, such as a catheter or inflatable balloon. During delivery of a balloon expandable device, the device may shift position on the balloon. For example, FIG. 1 depicts a diagram of a stent 10 positioned on a balloon 12 disposed on a catheter 14. As it is delivered into a bodily lumen, stent 10 may tend to shift. For instance, stent 10 may shift along the cylindrical axis of balloon 12 as depicted by an arrow 16. In addition, the device may shift enough that the device becomes separated from the balloon. Both of these cases negatively impact a treatment with the implantable medical device.

Figure 2:
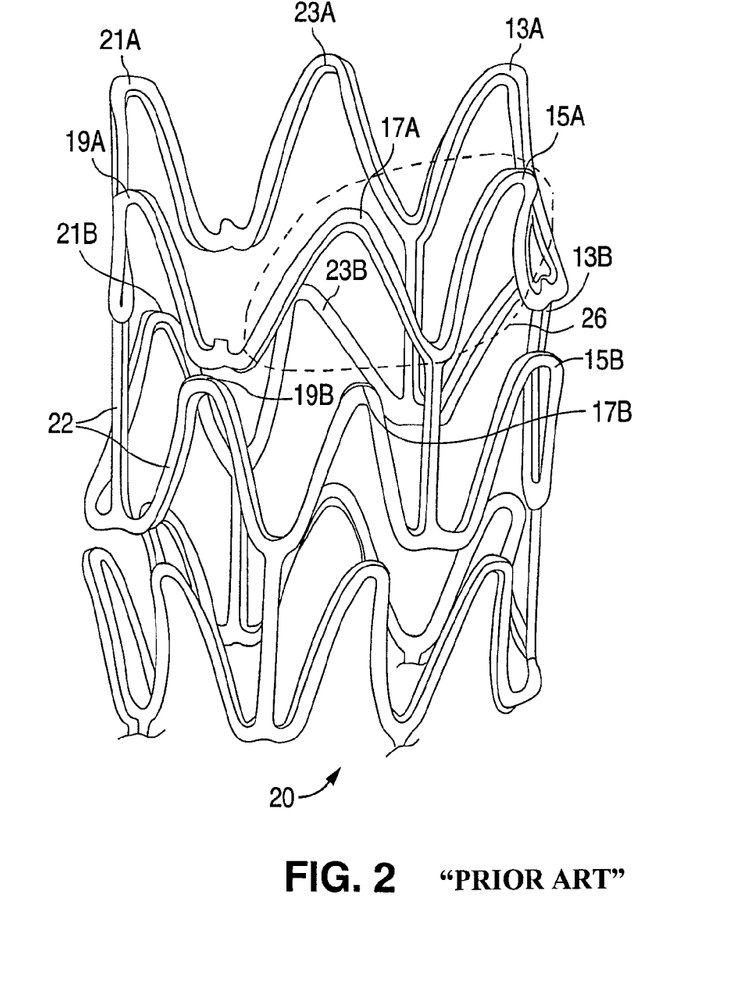
FIG. 2 depicts a stent.
Figure 3:
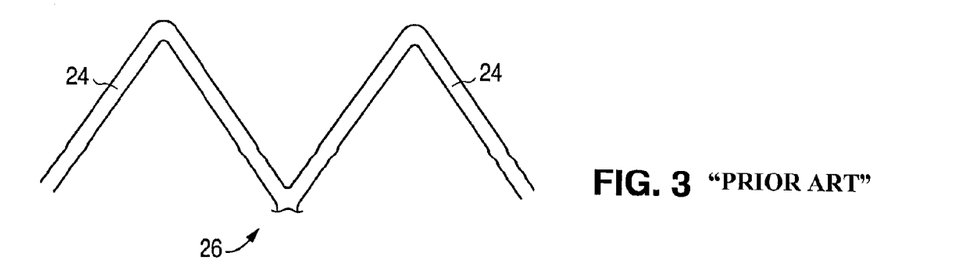
FIGS. 3 and 4 depict structural elements of a stent.
Figure 4:
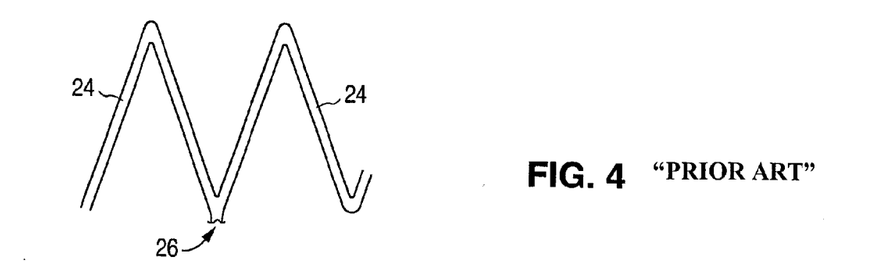

An implantable medical device, such as a stent, may be composed of a network or pattern of interconnecting structural elements or struts. For example, FIG. 2 depicts an implantable medical device 20 that includes structural elements 22. The implantable medical device may be configured to be radially expandable to enable deployment of the device into a bodily lumen. A cylindrical or substantially cylindrical implantable medical device may be fabricated with an inside diameter greater than the outside diameter of a delivery implement to facilitate positioning the device on the delivery implement. An implantable medical device may be positioned on the delivery implement and compressed or crimped to a delivery diameter. "Delivery diameter" refers to a diameter at which a cylindrical or substantially cylindrical implantable medical device, such as a stent, is introduced and transported in a bodily lumen. Therefore, the device may be configured to be radial compressible as well. FIG. 3 depicts a section 26 from implantable medical device 20 with structural elements 24. In some embodiments, FIG. 3 may depict a configuration of section 26 prior to crimping of an implantable medical device. Crimping implantable medical device 20 may cause structural elements 24 of section 26 to contract, as shown in FIG. 4. Before deployment, it may be desirable to secure the implantable medical device to the delivery implement.

In certain embodiments, an implantable medical device configured to be secured on a delivery implement may include a network of interconnecting structural elements. In some embodiments, the network may be substantially cylindrical. The implantable medical device may be an expandable stent. In addition, the delivery implement may correspond to an inflatable balloon. The network may be configured to be positioned on a delivery implement. The device may also include a first coupling element connected to the network and a second coupling element connected to the network. In some embodiments, the first coupling element and the second coupling element may be adapted to be releasably coupled. The releasably coupled elements may be adapted to inhibit shifting of the network positioned on the delivery implement. In one embodiment, the releasably coupled elements may be further adapted to inhibit separating of the network from the delivery implement.

Various embodiments of a method of securing the implantable medical device on a delivery implement are described herein. Certain embodiments of the method may include positioning the implantable medical device on a delivery implement. The implantable medical device may include a first coupling element and a second coupling element. The method may further include compressing the implantable medical device positioned on the delivery implement. Compressing may correspond to crimping an implantable medical device on a delivery implement. An embodiment of the method may further include releasably coupling the first coupling element to the second coupling element. The coupling elements may be configured to be releasably coupled contemporaneous with or subsequent to compressing of the implantable medical device.

"Releasably coupled" elements may refer to elements fastened together that are configured to decouple or separate upon exposure to one or more selected conditions. In one embodiment, releasably coupled elements may be configured to separate upon application of a force above a selected value or range. In other embodiments, releasably coupled elements may be configured to separate upon exposure to a selected temperature range and/or chemical environment. The separation can include a clean or relatively clean separation between the two elements. A clean or relatively clean separation may refer to a separation in which the structure of the coupling elements after separation is the same or substantially the same as it was before engagement. Alternatively, one or more conditions may cause fracturing of a portion of the first coupling element and/or the second coupling element. Separation of the coupling elements may be due to fracturing of a portion of the first coupling element and/or the second coupling element at or proximate a zone comprising the fracturing. The separation may include a fracture of a part of an element such that the fractured part should remain connected to the other element. A fractured or unclean separation may typically occur when force is used as a means of release.

In some embodiments, the method may further include delivery of the implantable medical device subsequent to releasably coupling the coupling elements. Delivery of the compressed implantable medical device may include introducing and transporting the device in a bodily lumen. In an embodiment, releasably coupled elements may be configured to remain substantially coupled when exposed to conditions during delivery of the implantable medical device. Therefore, the releasably coupled elements may inhibit shifting of the device on the delivery implement during delivery. In addition, the releasably coupled elements may inhibit separating of the device from the delivery implement during delivery. The releasably coupled elements may also be adapted to inhibit expansion of a self-expanding implantable medical device, such as a self-expanding stent.

Additionally, the device may be deployed at a selected treatment site in a bodily lumen. The delivery implement may be configured to decouple or separate the first coupling element from the second coupling element to allow deployment of the implantable medical device. The delivery implement may expand the compressed implantable medical device at a selected site within a bodily lumen. The expansion of the delivery implement may apply a force to the compressed implantable medical device and the coupled elements. In some embodiments, the applied force may be sufficient to decouple or separate the first coupling element from the second coupling element. The delivery implement may expand a cylindrical or substantially cylindrical implantable medical device at a treatment site to a selected diameter, which is a deployment diameter.

Various embodiments of the method may include alternative modes of releasably coupling the first coupling element to the second coupling element. In one embodiment, releasably coupling the first coupling element to the second coupling element may include engaging the first coupling element with the second coupling element. As used herein, "engaging" refers to bringing the coupling elements together. In some embodiments, engaging the coupling elements may be sufficient to releasably couple the elements within a selected range of conditions. For example, the elements can be designed to be friction fitted within one another. Alternatively, engaging the elements may be insufficient to releasably couple the elements. Therefore, some embodiments may further include releasably locking the engaged coupling elements. Releasably locking may refer to treating the engaged coupling elements with a procedure that releasably couples the engaged coupling elements. For example, releasably locking may include laser welding the engaged coupling elements. Alternatively, the engaged elements may be treated with a solvent or adhesive that locks or bonds together engaged coupling elements. "Solvent" is defined as a substance capable of forming a liquid or semi-liquid form of the material from which the coupling elements are made from at the interfacing surfaces of the coupling elements to allow conjoining of the elements. Once the solvent is removed, the elements should remain conjoined to one another.

Figure 5:
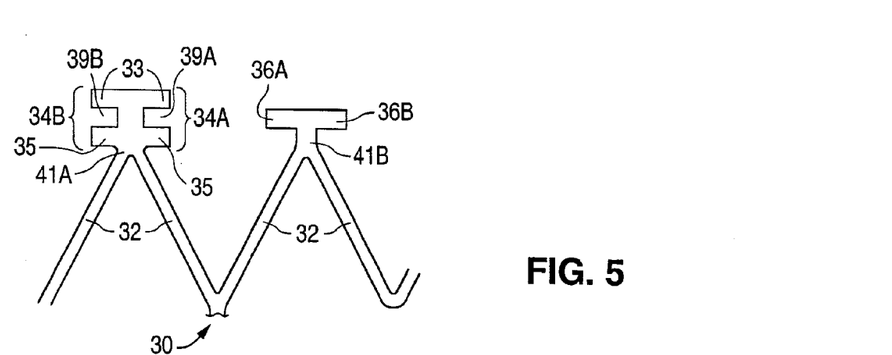
FIG. 5 depicts structural elements of a stent including coupling elements in an open or released position.
Figure 6:
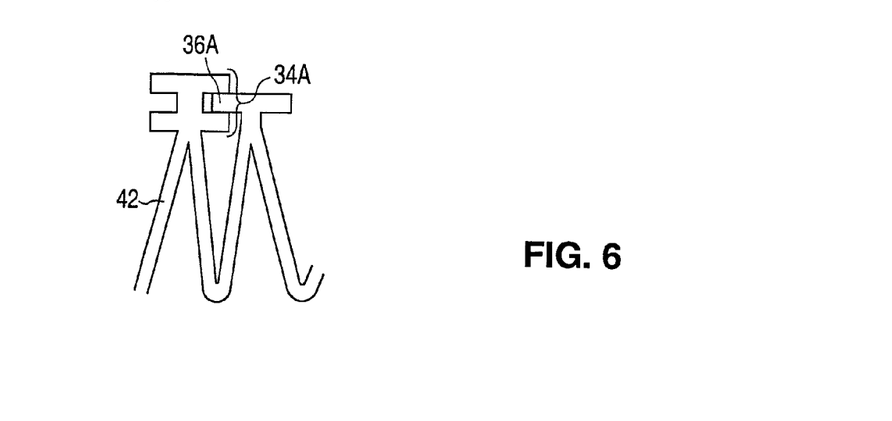
FIG. 6 depicts structural elements of a stent including coupling elements in a closed or locked position.

In certain embodiments, the first coupling element and the second coupling element may include complementary shapes configured for mating. For instance, the first coupling element may include a male end and the second coupling element may include a female end. Engaging the coupling elements may correspond to mating the male end with the female end. In general, a male end may include a shape that is configured to least partially penetrate or interdigitate within a complementary shape at a female end. The male end, for example, may be a rectangular or other similarly shaped tab. The female end may include a cavity formed by other similarly shaped tabs. FIG. 5 depicts a section 30 of an implantable medical device with structural elements 32, coupling elements 34A and 34B, female ends, and coupling elements 36A and 36B, male ends. The coupling elements are located proximate to nodes 41A and 41B of structural elements 32. Coupling element 34A includes separated tabs 33 and 35 which form gap 39A, giving the couplings an "H" shape. Coupling element 36A is a rectangular-shaped tab or member that is configured to engage coupling element 34A at gap 39A. FIG. 5 depicts the coupling elements in an unmated or unengaged configuration. In one embodiment, crimping or compressing an implantable medical device may contract the structural elements that make up the device. In certain embodiments, the crimping or compressing may cause coupling elements to engage. FIG. 6 depicts the coupling elements 34A and 36A in an engaged configuration. Coupling element 34A is mated with coupling element 36A. The degree of mating or engagement is partial since coupling element 36A does not completely fill gap 39A. In one embodiment, coupling element 34A and coupling element 36A may be releasably locked after engaging. Alternatively, coupling element 34A and coupling element 36A may be releasably locked by applying a locking procedure such as laser welding. As described above, coupling element 34A and coupling element 36A may be configured to decouple or separate, for example, upon exposure to a force within a given range.

The shapes of coupling elements are by no means limited to those illustrated in FIGS. 5 and 6. A large variety of complementary shapes may be configured for mating. Generally, a first coupling element may include at least one shape that is complementary to at least one shape of a second coupling element. The first coupling element and the second coupling element may be configured to allow at least some engagement of the two elements. Male coupling elements may include "U-" shaped elements, cylindrical-shaped elements, conical-shaped elements, curved elements, oval-shaped elements, and many others. In addition, combinations of shapes may be also be implemented. Female elements may be configured to complement the male elements to allow at least some engagement of the male and female elements.

In addition, a coupling element may each include both male and female structures. Complementary coupling elements may each include multiple tabbed-elements such as plug-shaped elements, serrated elements, sawtooth elements, or combinations of shapes listed above. For example, a first coupling element may include a first sawtooth structure and a second coupling element may include a second sawtooth structure. The first sawtooth structure and the second sawtooth structure may be configured to allow at least some engagement of the two structures.

In certain embodiments, the first and/or second coupling elements may be a planar or substantially planer surfaces. The surfaces may be formed to have a degree of roughness to facilitate releasably coupling the elements.

Various embodiments of the implantable medical device and method may include various locations of the first coupling element and the second coupling element on the implantable medical device. The coupling elements may be located on a proximal or distal end of a device. For example, as indicated in FIG. 2, a first coupling element may be at a location 21A and a second coupling element may be at a location 23A. Additionally, the coupling elements may be located between a proximal end and a distal end of a device. For instance, a first coupling element may be at a location 19B and a second coupling element may be at a location 17B.

An implantable medical device may be described more generally as including at least two coupling elements, as shown in FIGS. 5 and 6. A method may be further be described as including releasably coupling at least one coupling element to another coupling element. Moreover, several embodiments of the method may include securing an implantable medical device using more than two coupling elements. Thus, an embodiment may include releasably coupling more than one set of coupling elements. Typically, a set of coupling elements may be a pair of coupling elements, one with a male end and one with a female end, as depicted in FIGS. 5 and 6. In an embodiment, alternating male and female ends can be distributed around the circumference of the device. For example, as indicated in FIG. 2, coupling elements may be at locations 13A, 15A, 17A, 19A, 21A, and/or 23A. Additionally, coupling elements may be at locations 13B, 15B, 17B, 19B, 21B, and/or 23B. Moreover, a coupling element may be configured to releasably couple to a coupling element on an adjacent location. For example, a coupling element at location 13A may be configured to releasably couple to a coupling element at location 15B, a coupling element at location 19A may be configured to releasably couple to a coupling element at location 21A, etc. Alternatively, a coupling element may be configured to releasably couple to a coupling element on a nonadjacent location. In some embodiments, at least two of the releasably coupled sets of coupling elements may be configured to collectively inhibit or prevent shifting of the implantable medical device on a delivery implement. The releasably coupled sets may also collectively inhibit or prevent separating of the device from the delivery implement.

Figure 7:
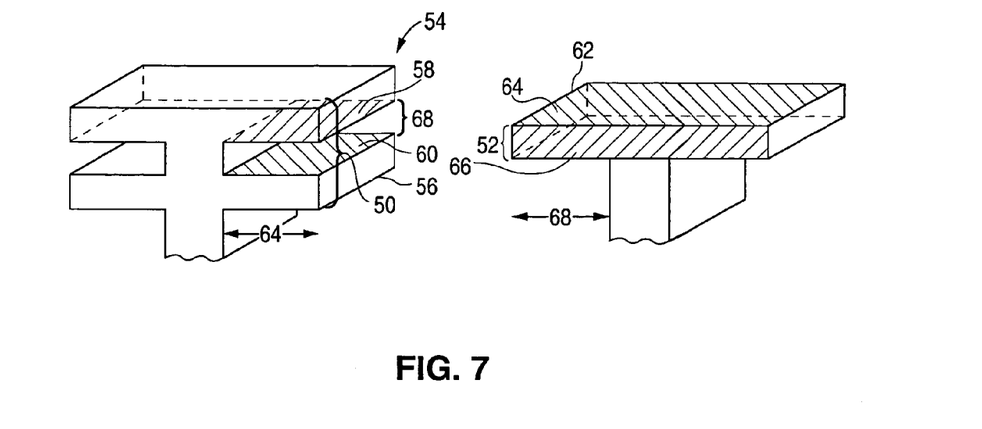
FIG. 7 depicts one embodiment of the coupling elements.

Additionally, the strength of the coupling or bond between the releasably coupled elements may depend on the engaged surface area. Generally, the larger the surface area engaged, the stronger the coupling between the coupling elements. For example, FIG. 7 depicts a coupling element 50 and a coupling element 52. Coupling element 50 has tabs 54 and 56 with surfaces 58 and 60, respectively. Coupling element 52 has tab 62 with surfaces 64 and 66. The strength of the coupling between coupling elements 50 and 52 may be optimized by increasing or decreasing the surface area of engagement of surfaces 58 and 60 with surfaces 64 and 66, respectively. In one embodiment, the surface area of engagement may be controlled by changing the degree of compression or crimping. Generally, however, an implantable medical device may have a desired configuration or crimped radius. The surface area of engagement for a given degree of crimping may be controlled by changing the potential surface area of engagement, e.g., surfaces 58, 60, 64, and 66.

For example, lengths 64 and 68 may be increased or decreased to change the potential surface area of engagement.

In general, it is not desirable for the coupling elements to prevent the implantable medical device from achieving a desired crimped radius. For example, tab 62 should not be configured to completely engage or fill gap 68 prior to a desired degree of crimping of a device. On the other hand, it is also desirable that a coupling element at least partially engage or interdigitate when the device is crimped to a desired diameter. For example, it is important for tab 62 be long enough to at least partially engage gap 68 at a desired degree of crimping.

Furthermore, the profile of coupling elements may be an important factor in the securing of an implantable medical device such as a stent to a delivery implement. The profile can influence the closeness of the fit of the device on a delivery implement and affect the blood flow around a device. The shape or curvature of coupling elements may be an important aspect of the profile. In some embodiments, a pair of coupling elements may be configured to conform or substantially conform to the shape of the device at a desired radius. For example, the coupling elements may be formed with a curved profile with a radius of curvature similar to that of a device at the desired radius. The curvature may follow the direction of engagement of the coupling elements. Alternatively, the pair of coupling elements may be "bent" or formed at an angle to follow the curvature of the device. Curved or bent coupling elements may present a smaller profile when implanted, and thus cause less of a disturbance to blood flow. In addition, curved or bent coupling elements may allow the device to fit more closely over a delivery implement than straight coupling elements.

Figure 8A:
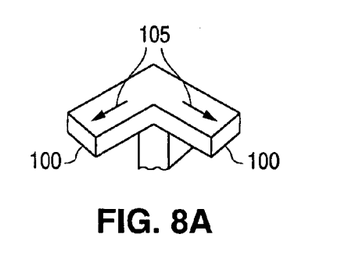
FIG. 8A depicts an example of a pair of coupling elements with a bent configuration.
Figure 8B:
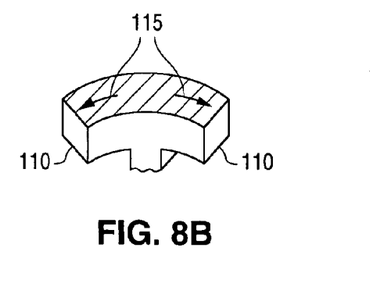
FIG. 8B depicts an example of a pair of coupling elements with a curved configuration.

FIG. 8A depicts an example of a pair of coupling elements 100 with a bent configuration. Coupling elements 100 are male coupling elements similar to coupling element 52 in FIG. 7. The arrows 105 represent the direction of engagement. FIG. 8B depicts an example of a pair of coupling elements 110 with a curved configuration. Coupling elements 110 are also male coupling elements. The curvature is along the direction of engagement and is shown by arrows 115. Coupling elements 100 and 110 are configured to engage female coupling elements with bent and curved configurations, respectively.

Figure 8C:
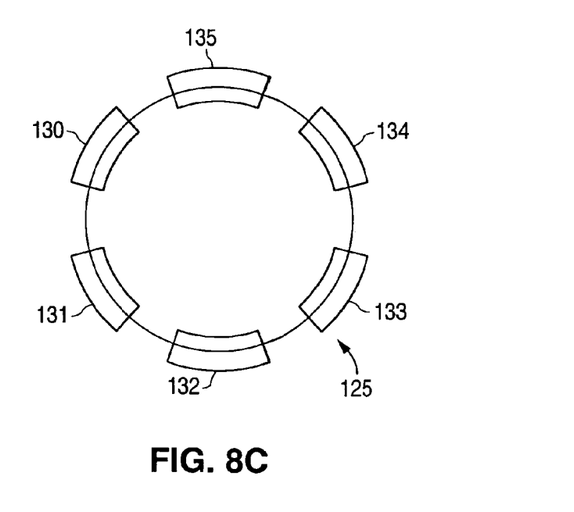
FIG. 8C depicts an axial view of a stent with curved pairs of coupling elements similar to the coupling elements in FIG. 8B.

FIG. 8C depicts an axial view of a stent 125 with curved pairs of coupling elements 130-135 similar to the coupling elements in FIG. 8B. Pairs of coupling elements 130, 132, 134 may be male coupling elements and pairs of coupling elements 131, 133, 135 may be female coupling elements.

Figure 9A:
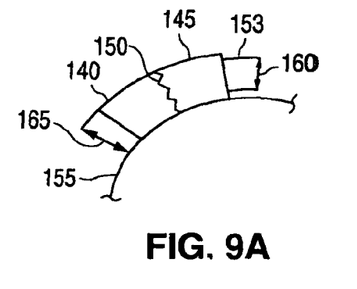
FIG. 9A illustrates a cross-section of a coupling element.

Additionally, the radial thickness of the coupling elements may affect the closeness of the fit of an implantable medical device such as a stent on a delivery implement and affect the blood flow around an implanted device. The radial thickness is the thickness of coupling elements in a direction perpendicular or substantially perpendicular to the axis of a device and the direction of engagement. When the radial thickness of the coupling elements is greater than the radial thickness of the structural elements of the device, the coupling elements may prevent contact with the device which prevents a close fit of the device on a delivery implement. FIG. 9A illustrates a cross-section of a coupling element 140 and a coupling element 145 that are engaged as indicated at an interface 150. Coupling elements 140 and 145 are configured to secure a stent on a delivery implement 155. A radial thickness 165 of coupling elements 140 and 145 is greater than radial thickness 160 of structural element 153. FIG. 9A shows that coupling elements 140 and 145 prevent a close fit of a stent on delivery implement 155.

Figure 9B:
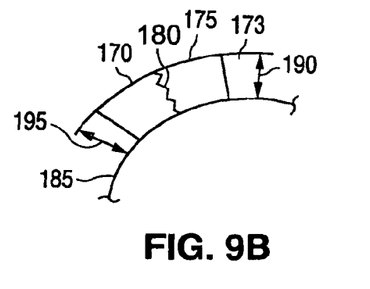
FIG. 9B illustrates a cross-section of a coupling element.
Figure 9C:
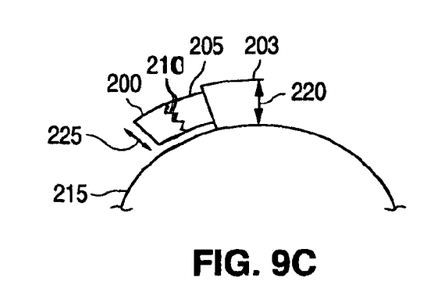
FIG. 9C illustrates a cross-section of a coupling element.

However, if the radial thickness of the coupling elements is less than, the same as, or approximately the same as the thickness of the structural elements of a stent, a close fit of the stent on the delivery implement may be achieved. It is expected that in this case, the disruption to blood flow will be less than when the radial thickness of the coupling elements is the greater than the radial thickness of the structural elements. FIG. 9B illustrates a cross-section of a coupling element 170 and a coupling element 175 that are engaged as indicated at interface 180. Coupling elements 170 and 175 are configured to secure a stent on delivery implement 185. A radial thickness 195 of coupling elements 170 and 175 is about the same as radial thickness 190 of a structural element 173. FIG. 9B illustrates that coupling elements 170 and 175 allow a close fit of a stent on delivery implement 185. FIG. 9C illustrates a cross-section of a coupling element 200 and a coupling element 205 that are engaged as indicated at interface 210. Coupling elements 200 and 205 are configured to secure a stent on delivery implement 215. A radial thickness 225 of coupling elements 200 and 205 is less than a radial thickness 220 of a structural element 203. FIG. 9C illustrates that coupling elements 200 and 205 allow a close fit of a stent on delivery implement 215.

Figure 10A:
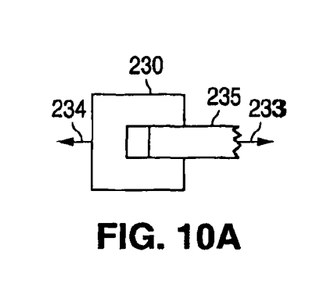
FIG. 10A depicts coupled elements.
Figure 10B:
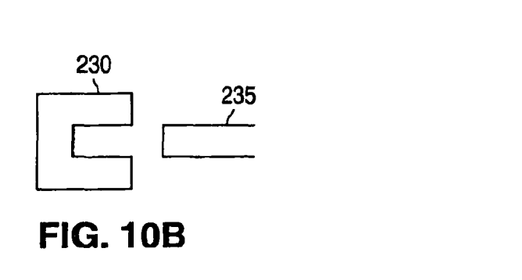
FIG. 10B depicts coupled elements of FIG. 10A separating by a clean separation upon application of a force.
Figure 10C:
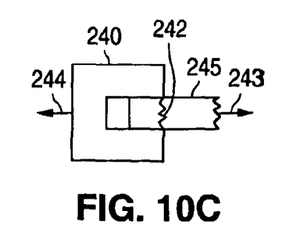
FIG. 10C depicts releasably coupled elements.
Figure 10D:
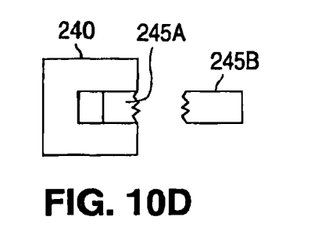
FIG. 10D depicts separation of coupling elements of FIG. 10C.

Furthermore, as indicated above, releasably coupled elements may release by a clean separation between coupled elements or separate due to fracture of part of an element. FIG. 10A depicts coupled elements 230 and 235. Upon application of a force, for example, as shown by arrows 233 and 234, coupled elements 230 and 235 separate by a clean separation, as shown in FIG. 10B. Alternatively, FIG. 10C depicts releasably coupled elements 240 and 245 with an applied force as shown by arrows 243 and 244. The force initiates a fracturing at a fracture zone 242. FIG. 10D depicts separation of coupling elements 240 and 245 at the region of fracture zone 242 that results in separation of coupling element 245 into a fragment 245A and a fragment 245B.

Implantable medical devices that include releasably coupled elements, such as those shown in FIGS. 5 and 6, may be fabricated by several methods. For example, laser cutting may be used to form a network of structural elements that includes releasably coupled elements. The network may be cut directly on a tube. Alternatively, the network may be cut in a sheet that may be formed into a tube. Other embodiments may include chemical etching the network on a sheet or a tube.

As described above, the engaged or mated coupling elements may be releasably coupled by locking the coupling elements. Laser welding of coupling elements is particularly desirable for use on polymeric implantable medical devices. Laser welding may include directing a laser beam at or near the point at which coupling elements are engaged. The laser beam may heat the polymer at or near the engagement point. At least some of the polymer at the engagement point may be melted. It may be desirable to provide heat sufficient to melt, but not vaporize the polymer. The coupling elements may then be welded by a laser, such as a $CO_2$ laser or YAG laser. A $CO_2$ laser may be particularly desirable since it is capable of providing heat localized to the engagement point. As a result, degradation of polymer due to heating may be minimized. Furthermore, a $CO_2$ laser does not emit light in the ultraviolet spectrum, which tends to degrade polymers.

Furthermore, one embodiment of a method of laser welding engaged coupling elements may include first compressing or crimping a stent. The crimped stent may then be disposed into a glass tube of an appropriate diameter. The glass tube prevents recoil or self-expansion of the stent so that communication between the coupling elements is maintained. For example, the inside diameter of the glass tube may be a desired diameter of the crimped stent. The laser light may pass through the glass tubing and be absorbed by the polymer. Therefore, the polymer may be welded inside of the glass tube. This procedure can be conducted subsequent to positioning the stent on the delivery implement.

In certain embodiments, the implantable medical device may be coated with a polymeric coating that includes an active agent or drug. Since active agents tend to degrade when exposed to elevated temperature, it may be advantageous to limit exposure of the active agent to the heat from the laser welding process. For example, some active agents tend to degrade at temperatures above about 80° C. Others may tend to degrade above about 100° C. In one embodiment, exposure of the active agent to elevated temperature may be reduced by not coating the coupling elements with a coating that includes a drug prior to the laser welding process. Alternatively, the implantable medical device may be coated subsequent to the laser welding process.

Additionally, an alternative method of releasably coupling engaged coupling elements may include applying a solvent at or near the engagement point of the coupling elements. The solvent may be capable of dissolving at least some of the polymer to form a polymer solution. The polymer solution may tend to flow at the engagement point. The formation and flow of the polymer solution may act to form a bond between the coupled elements once the solvent is removed. All or a majority of solvent may be removed by blowing an inert gas on the coupled elements. Representative examples of inert gases include nitrogen, argon, etc. In addition, solvent may be removed by heating the implantable medical device to a temperature range below a degradation temperature range of an active agent. All or a majority of the solvent may also be removed by exposing the device with the coupling elements to a vacuum.

Additionally, another method of releasably coupling engaged coupling elements may include applying an adhesive at or near the engagement point of the coupling elements. In one embodiment, the applied adhesive may be dissolved in a solvent. For instance, the adhesive may be a biostable or biodegradable polymer in solution. Other biodegradable materials may be used. The solvent may be removed using the methods described above. Representative solvents that may be used include chloroform, polyethylene glycol, and/or other biocompatible solvents.

EXAMPLE

Some embodiments of the present invention are illustrated by the following Example. The Example is being given by way of illustration only and not by way of limitation. The Example illustrates the implantable medical device described herein capable of being secured. The Example also illustrates the method described herein of securing the implantable medical device. The parameters and data are not to be construed to unduly limit the scope of the embodiments of the invention.

An implantable medical device, or stent, was fabricated according to the methods described herein. An uncoated polymeric stent was used for this example. The stent was fabricated from poly(L-lactic acid). The stent network with coupling elements was fabricated by laser cutting a tube. The coupling elements were fabricated on the nodes of structural elements at a proximal or distal end of the stent. After fabrication, the stent was positioned on an inflatable balloon.

Figure 11:
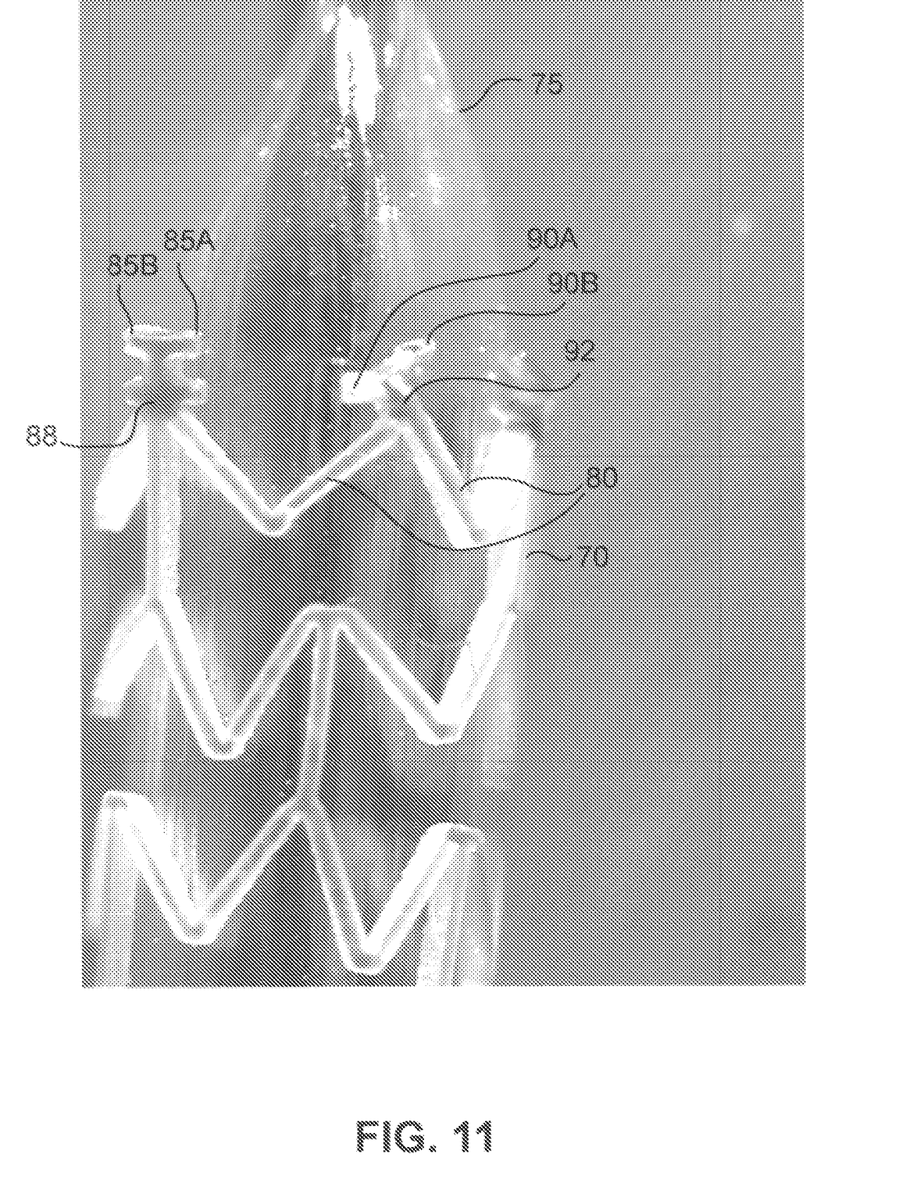
FIG. 11 depicts an optical micrograph of a stent with structural elements positioned on a balloon in a configuration prior to crimping.
Figure 12:
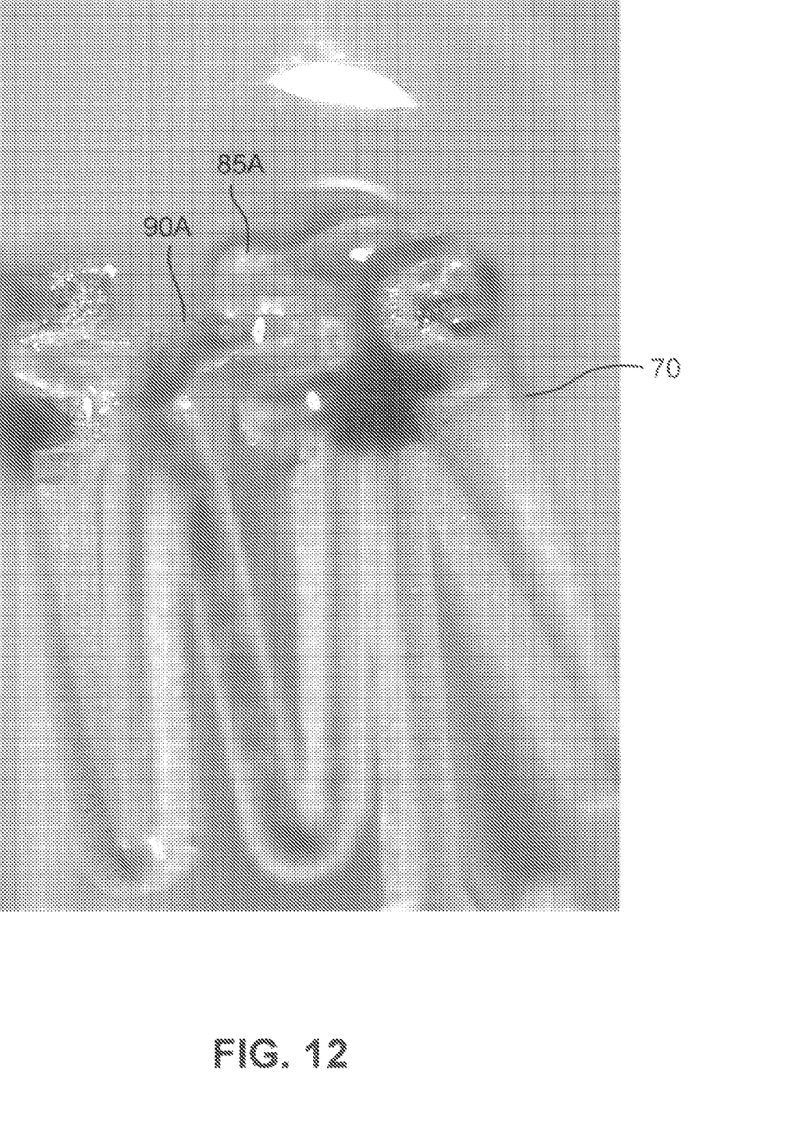
FIG. 12 depicts a stent subsequent to crimping on a balloon.

FIG. 11 depicts an optical micrograph of a stent 70 with structural elements 80 positioned on a balloon 75 in a configuration prior to crimping. The stent has female coupling elements 85A and 85B proximate to node 88. The stent also has male coupling elements 90A and 90B proximate to node 92. FIG. 12 depicts stent 70 subsequent to crimping on balloon 75. A standard crimper was used without heating. Coupling element 90A is shown engaged with coupling element 85A. Coupling elements at various nodes at the end of the stent were similarly engaged. The coupling elements were then releasably coupled by laser welding with a $CO_2$ laser. The releasably coupled elements were configured to decouple or separate upon inflation of the balloon.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A radially expandable implantable medical device, comprising:
   a stent configured to be secured on a delivery implement at a reduced diameter, wherein the stent includes first and second structural elements and first and second coupling elements,
   wherein the first coupling element is connected to the first structural element and the second coupling element is connected to the second structural element,
   wherein the first coupling element and the second coupling element are located on a proximal end or a distal end of the stent on a node of the first structural element and a node of the second structural element,
   wherein the first and second structural elements bend at the nodes to allow contraction of the stent, and
   wherein the first coupling element is releasably coupled directly to the second coupling element, compressing the stent to the reduced diameter releasably couples the first coupling element directly to the second coupling element, and wherein the first coupling element and the second coupling element form releasably directly coupled elements.

2. The device of claim 1, wherein the first coupling element and the second coupling element conform to a shape of the stent.

3. The device of claim 1, wherein a radial thickness of the first coupling element and a radial thickness of the second coupling element is less than a radial thickness of at least one structural element of the stent.

4. The device of claim 1, wherein a radial thickness of the first coupling element and a radial thickness of the second coupling element is equal to a radial thickness of at least one structural element of the stent.

5. The device of claim 1, wherein a radial thickness of the first coupling element and a radial thickness of the second coupling element are greater than a radial thickness of at least one structural element of the stent.

6. The device of claim 1, wherein the stent is configured to be secured on a delivery implement that comprises an inflatable balloon.

7. The device of claim 1, wherein the releasably coupled elements are adapted to inhibit or prevent shifting of the stent on the delivery implement or to inhibit or prevent separating of the stent from the delivery implement.

8. The device of claim 1, wherein the releasably coupled elements are configured to release upon exposure to one or more conditions.

9. The device of claim 8, wherein the release of the releasably coupled elements comprises a clean or substantially clean separation of the releasably coupled elements, and wherein a structure of the releasably coupled elements after separation is the same or substantially the same as it was before coupling.

10. The device of claim 8, wherein at least one condition is selected from the group consisting of a selected range of force, a selected temperature range, and a selected chemical environment.

11. The device of claim 1, wherein the stent is configured to be secured on a delivery implement configured to apply a force to the stent sufficient to separate the first coupling element from the second coupling implement.

12. The device of claim 1, wherein the releasably coupled elements comprise engaged elements.

13. The device of claim 1, wherein the releasably coupled elements are adapted to inhibit expansion of the stent.

14. The device of claim 1, wherein the first coupling element comprises a male end and the second coupling element comprises a female end.

15. The device of claim 1, wherein the first coupling element comprises a first rectangular member, and wherein the second coupling element comprises a second rectangular member, a third rectangular member, and a fourth rectangular member configured to form a cavity that allows at least partial penetration of the first rectangular member.

16. The device of claim 1, wherein the first coupling element comprises a U-shaped member and the second coupling element comprises a member comprising a U-shaped cavity that allows at least partial penetration of the U-shaped member.

17. The device of claim 1, wherein the first coupling element comprises a first surface with a least three projections that form at least two cavities and the second coupling element comprises a second surface with at least three projections that form at least two cavities, wherein at least two projections on the first surface are configured to at least partially penetrate at least two cavities on the second surface, and wherein at least two projections on the second surface are configured to at least partially penetrate at least two cavities on the first surface.

18. A radially expandable implantable medical device, comprising:
a stent configured to be secured on a delivery implement at a reduced diameter, wherein the stent includes first and second structural elements and first and second coupling elements,
wherein the first coupling element is connected to the first structural element and the second coupling element is connected to the second structural element,
wherein the first coupling element and the second coupling element are located on a proximal end or a distal end of the stent on a node of the first structural element and a node of the second structural element,
wherein the first and second structural elements bend at the nodes to allow contraction of the stent, and wherein the first coupling element is releasably coupled to the second coupling element, compressing the stent to the reduced diameter releasably couples the first coupling element to the second coupling element, and wherein the first coupling element and the second coupling element form releasably coupled elements,
wherein the first coupling element comprises a first sawtooth structure and the second coupling element comprises a second sawtooth structure, wherein the first sawtooth structure and the second sawtooth structure are configured to allow at least some engagement of the first and second sawtooth structures.

19. A radially expandable implantable medical device, comprising:
a stent including first and second structural elements and first and second coupling elements,
wherein the stent has a fabricated diameter and a delivery diameter,
wherein the first coupling element is connected to the first structural element and the second coupling element is connected to the second structural element,
wherein the first coupling element and the second coupling element are located on a proximal end or a distal end of the stent on a node of the first structural element and a node of the second structural element,
wherein the first and second structural elements bend at the nodes to allow contraction of the stent, and
wherein when the stent is compressed from the fabricated diameter to the delivery diameter over a delivery implement, the first coupling element is releasably coupled directly to the second coupling element, and wherein the first coupling element and the second coupling element form releasably directly coupled elements.

20. The device of claim 19, wherein the delivery implement comprises an inflatable balloon.

21. The device of claim 19, wherein the releasably coupled elements are adapted to inhibit or prevent shifting of the stent on the delivery implement or to inhibit or prevent separating of the stent from the delivery implement.

22. The device of claim 19, wherein the delivery implement is configured to apply a force to the stent sufficient to separate the first coupling element from the second coupling implement.

23. The device of claim 19, wherein the releasably coupled elements comprise engaged elements.

24. The device of claim 19, wherein the releasably coupled elements are adapted to inhibit expansion of the stent.

25. The device of claim 19, wherein the first coupling element comprises a male end and the second coupling element comprises a female end.

26. The device of claim 19, wherein the first coupling element comprises a first rectangular member, and wherein the second coupling element comprises a second rectangular member, a third rectangular member, and a fourth rectangular member configured to form a cavity that allows at least partial penetration of the first rectangular member.

27. The device of claim 19, wherein the first coupling element comprises a first surface with a least three projections that form at least two cavities and the second coupling element comprises a second surface with at least three projections that form at least two cavities, wherein at least two projections on the first surface are configured to at least partially penetrate at least two cavities on the second surface, and wherein at least two projections on the second surface are configured to at least partially penetrate at least two cavities on the first surface.

* * * * *